United States Patent [19]

Lundberg et al.

[11] Patent Number: 4,641,969
[45] Date of Patent: Feb. 10, 1987

[54] METHOD AND APPARATUS FOR MEASURING THE CONTENT OF SUSPENDED SUBSTANCES IN A FLOWING MEDIUM

[75] Inventors: Krister Lundberg; Göran Tidstam, both of Säffle, Sweden; Daniel F. Pope, Issaquah, Wash.

[73] Assignee: AB Bonnierforetagen

[21] Appl. No.: 641,953

[22] PCT Filed: Dec. 15, 1983

[86] PCT No.: PCT/SE83/00458

§ 371 Date: Aug. 14, 1984

§ 102(e) Date: Aug. 14, 1984

[87] PCT Pub. No.: WO84/02396

PCT Pub. Date: Jun. 21, 1984

[30] Foreign Application Priority Data

Dec. 15, 1982 [SE] Sweden .............................. 8207180

[51] Int. Cl.[4] .............................................. G01N 21/00
[52] U.S. Cl. ...................................... 356/343; 356/342
[58] Field of Search ........................... 356/341–343, 356/442; 250/574

[56] References Cited

U.S. PATENT DOCUMENTS

| | | | |
|---|---|---|---|
| 3,714,444 | 1/1973 | Carr et al. | 356/442 |
| 3,787,703 | 1/1974 | Topol | 250/574 |
| 3,906,241 | 9/1975 | Thompson | 250/574 |
| 4,193,692 | 3/1980 | Wynn | 356/341 |
| 4,290,695 | 9/1981 | Schmitt | 356/341 |

*Primary Examiner*—R. A. Rosenberger
*Assistant Examiner*—Crystal D. Cooper
*Attorney, Agent, or Firm*—Ostrolenk, Faber, Gerb & Soffen

[57] ABSTRACT

The present invention relates to a method and apparatus for measuring the content of suspended substances in a flowing medium by illuminating the medium with light from a light source. Reflected light from the medium is detected by at least two detectors, at least one of which measures directly reflected light while the other detectors measure multiply reflected light. The detector for detecting directly reflected light is located such that a linear relationship is established between its output signal and the concentration of the flowing medium. The other detectors are located such that their output signals will be essentially constant in relation to the concentration of particles in the flowing medium within a large range. The measuring scheme provides for obtaining the quotient of the signal provided by direct reflection divided by the signal provided by multiple reflection. A measure of concentration of the flowing medium is provided which is independent of disturbing factors such as for example pulp color.

14 Claims, 9 Drawing Figures

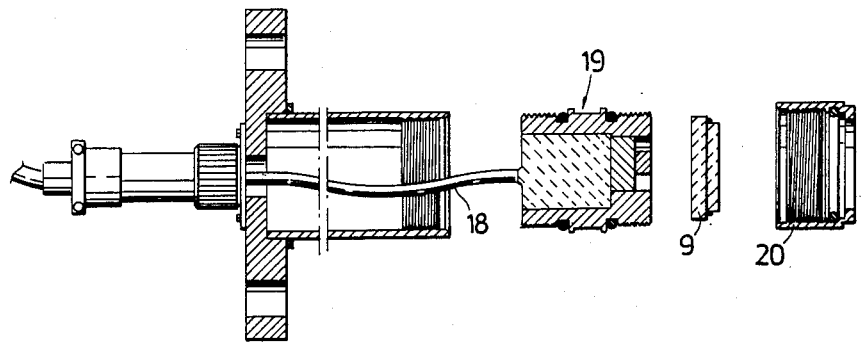
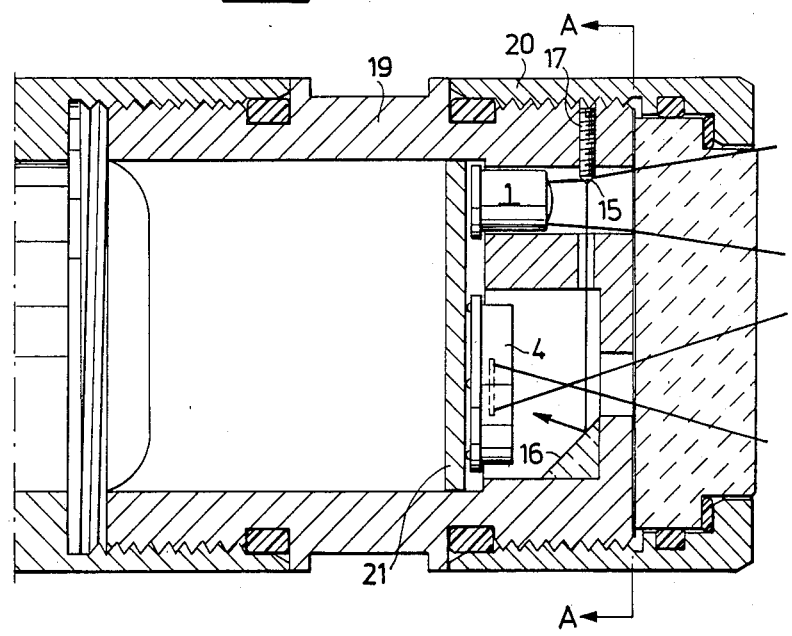

METHOD AND APPARATUS FOR MEASURING THE CONTENT OF SUSPENDED SUBSTANCES IN A FLOWING MEDIUM

BACKGROUND OF THE INVENTION

The present invention relates to a method and an apparatus for measuring the concentration of suspended substances in a flowing medium by illuminating the medium with light from a light source to detect light reflections which are indicative of particle concentration. The reflected light is detected in at least two detectors; the other for measuring directly reflected light and one for measuring multiply reflected light. Directly reflected light [refers to] [the] light received from an area of the medium that is directly illuminated by the light source and multiply reflected light is light received from an area of the medium that is rather not directly illuminated, but is illuminated by light that has been scattered from the direct beam. The apparatus is preferably intended for use in so-called consistency measurements, i.e. measurements of the content of fibres in fibre suspensions, such as is found in the pulp and paper industry. The consistency is defined as the weight of fibres per volumetric unit. It is therefore a definition of concentration of suspended solids, and will be so referred to, since the present invention may be used to measure any material that scatters light in the flowing medium.

A number of different methods have been developed for measuring the concentration of fibres in fibre suspensions. The primary methods are based on mechanical principles. In particular, a shear force principle particularly has come into use during the last 50 years. In shear force measurements, the network strength of the fibre suspension is measured first with the aid of a blade, a rotating sensor or the like. The relationship between the concentration and the network strength is then calculated by a special calibration method. More recently, however, optical methods have emerged. There are several reasons for of optically based methods. Firstly, the mechanical meters of the shear force or viscosity type normally require a great deal of maintenance. Secondly, the accuracy, particularly with stationary measurement, is relatively poor with mechanical apparatus. Thirdly, great technical advances were made in the optical and electronic fields, particularly in the latter, which have facilitated and reduced the cost of meters based on optical principles. Also, an accuracy may be obtained with electro-optical techniques which is at least as good as, and in some cases better than, that obtained with corresponding mechanical apparatus.

The disadvantage of electro-optical methods has, however, been the difficulty of measuring higher concentrations. One has therefore normally been limited to measurements in the range under 10 g/liter (1%). This is due to the fact that the primary choice has been to use transmission measurement, i.e. light transmitted through the fibre suspension is detected, rather than light reflected from the suspension. Since the intensity of the light passing through the suspension declines according to an exponential function, the signal that can be generated from the light is close to the signal noise threshold for even relatively low concentrations. Devices based on polarized transmitted, light also suffer from the same limitation.

SUMMARY OF THE INVENTION

The present invention relates to a method and apparatus of the type mentioned above, but are distinguished in that the detector for the directly reflected light is arranged at such a distance from the light source that a linear relationship exists between the output signal from the detector and the concentration parameter. The measured concentration parameter of the flowing medium vary linearly up to a maximum value of concentration. Beyond the maximum value, the signal from the detector does not increase even though the concentration is higher than second. A detector for detecting the multiply reflected light is disposed at a different location in relation to the light source such that its output signal will be independent of the concentration of the flowing medium within a large interval. An output is then obtained which comprises the ratio of the signal provided by direct reflection detect divided by the signal generated from the multiple reflected light. This output signal is directly related to and comprises a measure of the particle concentration in the flowing medium.

With the aid of the present invention the disadvantages of prior art concentration transducers is avoided in that reflected light is used for effecting the measurements. Prior art measurements provide good accuracy at concentrations well above the 1% level. But with the present invention concentrations of 6% may be measured without deteriorated accuracy. On some types of pulp fibre good linearity continues to 10% concentration or more.

BRIEF DESCRIPTION OF THE DRAWINGS

The invention will now be described below in detail with reference to the appended drawings.

FIG. 3 is a side view in section, on an enlarged scale, of an insertion probe included in another embodiment of the invention, FIG. 4 is a longitudinal section on enlarged scale, through the outer end of the insertion probe.

DETAILED DESCRIPTION

Figure 1:
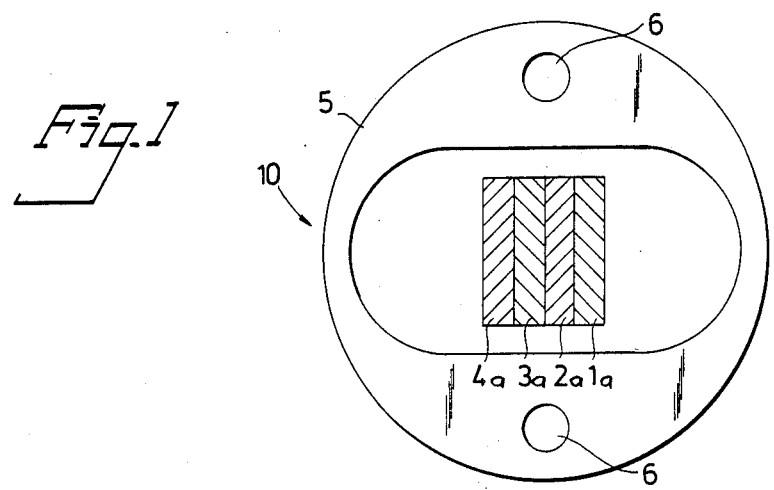
FIG. 1 is a section through a measuring head or insertion probe in a measuring apparatus according to an embodiment of the invention.
Figure 2:
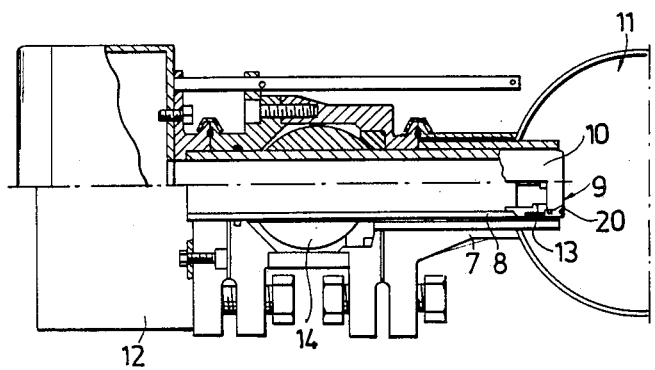
FIG. 2 is a side view, partly in section, of two designs of measuring apparatus according to the invention.
Figure 1A:
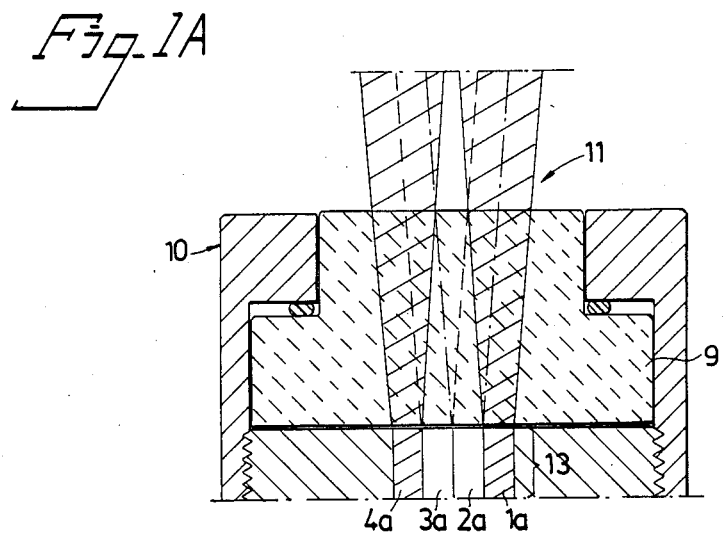
FIG. 1A is a side view section of the probe showing the beam of illumination from the light source and to the detectors.

In the embodiment illustrated in FIG. 1, a measuring head or insertion probe 10 includes four fields, field 1a assigned to a light source 1, field 2a assigned to a detector 2 intended for intercepting direct reflection and fields 3a, 4a, assigned to detectors 3, 4 for multiple reflection. These fields comprise one end 13 of optical fibre conductors. The end 13 includes a window 9, behind which is located a flange 5 attached to the end portion with the aid of attached screws (not shown) in attachment holes 6. The flange 5 is intended to center and fix the optical fibre conductors. The apparatus functions in the following manner. Light is directed through an optical fibre conductor and through the field 1a towards the fibre suspension that flows in pulp line 11 (see FIG. 2). The reflected light is detected in three different detectors 2–4 via fields 2a–4a, which are located at different spaced locations from field 1a while emits the light light source generated by a. The detector field 2a, which is nearest to the field 1a, primarily intercepts directly reflected light for measurement by the detector 2. The other two detector fields 3a and 4a accept light for measurement by the detectors 3, 4. The light that is intercepted and flows into fields 3a and 4a is reflected a number of times in the fibre suspension which and is therefore referred to as multiply reflected light. The beam of illumination from field 1a into stock line 11 through the window 9 is shown in FIG. 1A. Also shown are the angles of view of detectors 2, 3, 4 through fields 2a, 3a, 4a. The angles of these light beams are selected through appropriate placement of the light source and detectors with respect to the ends of the optical fibre conductors inside a casing 12.

As shown, the angle of view for detector 2 always intercepts some part of the direct illumination in the flowing medium regardless of the depth of penetration of the illumination, which decreases with increasing concentrations. Detector 3 is barely able to receive a direct reflection except at low concentrations. As is shown by shaded lines, the angle of view of detector 4 is arranged not to detect direct illumination of the medium at concentration levels encountered in applications related to the present invention.

Because the field of view of detector 2, is closest to the light source field 1a, the detector 2 will respond more or less linear output to the concentration levels of up to a maximum, in proportion to the reflectance of the medium. The detector 3 will also respond linearly to concentration (C), up to a maximum, which also is proportional to the reflectance, and then will begin to decrease linearly with C. Above the maximum the detector response will be approximately constant over a wide interval of concentration levels. The detector 4 will provide an output similar to that from detector 3, but will reach a maximum at a lower concentration and decrease linearly with increasing C but more rapidly than detector 3.

If the detectors 2, 3, 4 respond linearly to light then, they will then output signals which are proportional to $I_1$ (which is a number indicated of the light directed into the particle suspension) and vary with concentration C as described above and illustrated in FIG. 8. By obtaining the quotient, for example $I_{21}/I_{41}$, variations in $I_1$ have no effect on the result. $I_{21}$ refers to the signal developed by detector 2 in response to the light it "see" while $I_{41}$ refers to the signal from detector 4. Also, attenuation in light caused by color in the medium or dirt on the window 9 will affect both detector outputs nearly equally, so that the result will not be affected thereby.

As previously mentioned, the light is directed out via optical fibres toward the pulp fibres and reaches the pulp via the window 9 in the probe 10. Likewise this light is reflected and channeled back to electronic transducers associated with detectors 2, 3, 4 located in the casing 12. The probe 10, accommodating the optical fibres via a probe tube 8 and terminating at common end 13, extends from the casing 12 to the pulp line 11 inside a protective tube 7. To allow cleaning of the probe 10 during operation, there is a sluice valve 14 in the protective tube 7. This valve is in an open position when the probe 10 is inserted, but closes when the probe 10 is removed from the tube 7 to thus seal against fibre suspension leakage. The optical fibres carrying respective light beam are separated by an intermediate wall in the form of a blind baffle, e.g. of metal.

The different parts forming the insertion probe 10 can be seen in the embodiment illustrated in FIGS. 3–7. An electrical cable 18 (FIG. 3) terminates in an optical unit (FIG. 4), which includes the light source 1 and the detectors 2–4. A window 9 is fastened against the unit 19 with the aid of a fastening sleeve 20.

FIG. 4 illustrates the manner in which window 9 is fixed with the aid of the fastening sleeve 20 to the optical unit 19, in which the light source 1 and the detector 4 are retained with the aid of a sealing fastening plate 21. A reflecting means 15 in the form of a tip of a screw 17 going through the wall of the probe 10 blocks a portion of the light flow from the light source 1. The screw tip 15 thus reflects a portion of the light coming from the light source 1 via a mirror 16 directly into the detector 4, giving rise to a signal which is added to the signal $I_{41}$ from the detector 4 according to the relationship $(I_{21}/I_{41}+k\cdot I_1)$, where the constant k is optically determined. "c" is the calculated or measured value of the actual concentration "C" in the particle suspension. Instead of the reflecting means 15, an extra detector can be arranged in the path of the light source 1, whereby the constant k in this case is set electronically. By this arrangement there is obtained the linearity for the concentration values C of the flowing medium, these values being mainly below 1%, as will be seen from the signal slots of FIG. 8.

Figure 5:
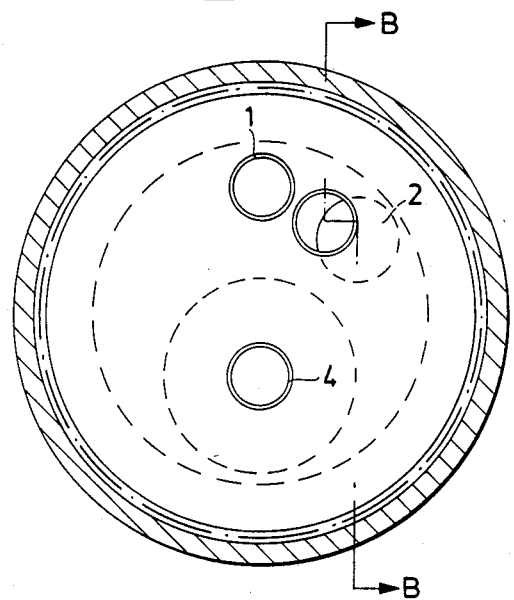
FIG. 5 is a cross section along line A—A through the outer end of the probe illustrated in FIG. 4.

FIG. 5, which is a section through the end of the probe 10 along line A—A in FIG. 4, shows the position of the light source 1 in relation to the detector 2 positioned to detect directly reflected light.

Figure 6:
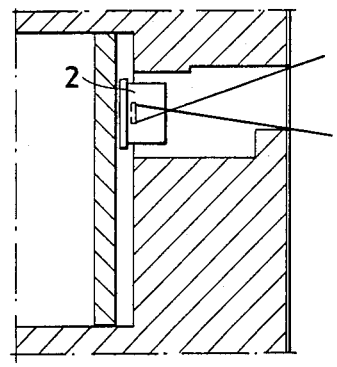
FIG. 6 is a partial section along the line B—B in the probe end illustrated in FIG. 5.

FIG. 6 is a section along the line B—B in FIG. 5 and illustrates that the light opening, through which light for detector 2 enters the device, to detector 2 is laterally displaced in relation to the location of detector 2 itself.

Figure 7:
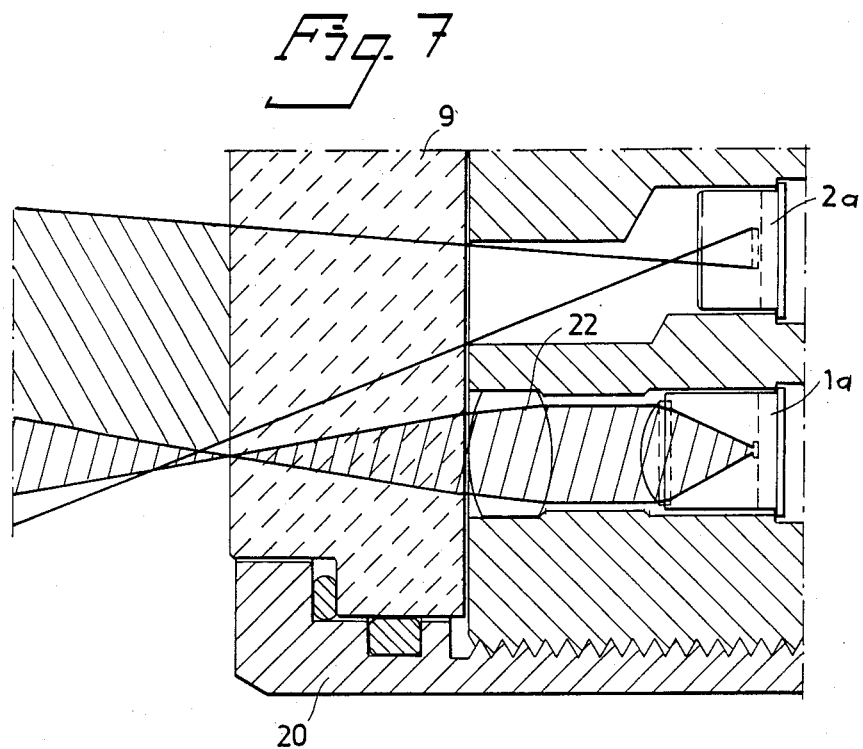
FIG. 7 is a partial view of a longitudinal section through another embodiment of the probe end.

In the embodiment illustrated in FIG. 7, a lens system 22 has been arranged in the beam path of the light source 1 between the window 9 and the source 1. The focal length of the lens system 22 is selected such that the light going through is focused at a point outside window 9. Thus, the measuring apparatus is insensitive to dirt which may cloud the window 9. Reflections can not directly reach detector 2 from the small area of the directly illuminated window surface.

Figure 8:
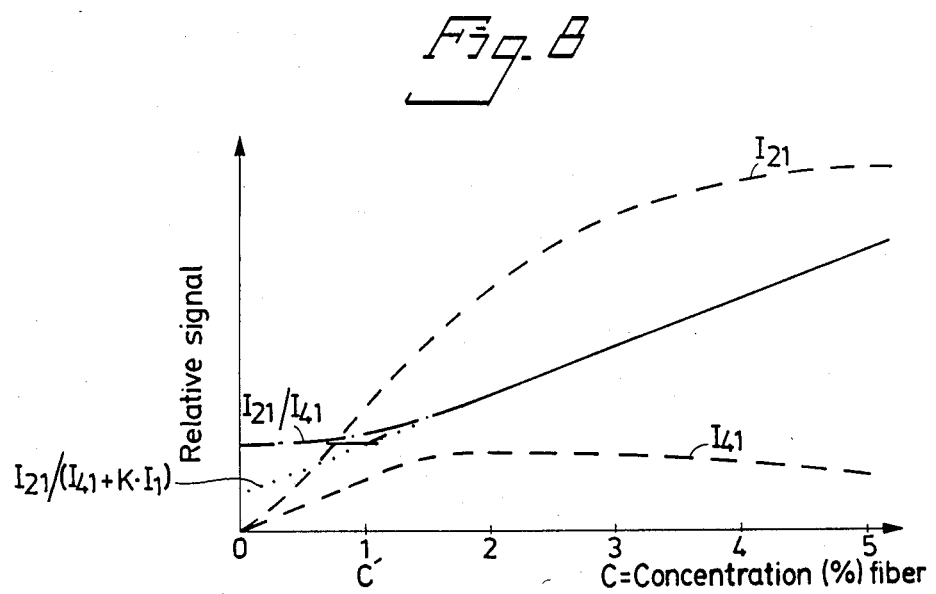
FIG. 8 illustrates the signals $I_{21}$, $I_{41}$, $I_{21}/I_{41}$ and $I_{21}/(I_{41}+k \cdot I_1)$ as a function of the concentration of the flowing medium.

FIG. 8 illustrates the different relative signals as a function of the fibre concentration C in the flowing medium. It can be seen that the relationship $I_{21}/I_{41}$ is substantially linear for fibre concentrations above a critical concentration C'. The relationship $c=I_{21}/(I_{41}+k\cdot I_1)$ provides a signal which is substantially linear for fibre concentrations both under and above the critical concentration C'.

Advantages obtained by adjustment of all the specified optical parameters include the extended linearity as compared with sensors using direct reflection alone, minimization of the effects of the medium color, surface dirt on window 9, and variations in light intensity $I_1$.

Electronic means for powering the light source and generating outputs from the detectors and combining them to obtain the necessary ratios and outputting scaled signals to display or control devices are shown to those skilled in the art. The present embodiments use, but are not restricted to, silicon photodiodes of large area in detectors 2, 3, 4 and a gallium arsenide light emitting diode of a 940 nm wavelength of operating in a pulsed manner in light source 1.

We claim:

1. A method for measuring the concentration of suspended particles in a flowing medium, comprising the steps of:
   directing a beam of light from a light source into the medium for producing directly reflected light which comprises light reflected from that portion of the medium which is illuminated directly by the beam of light and for producing multiply reflected light which comprises light reflected from areas of the medium into which the beam of light has scattered;
   intercepting the directly reflected light in a first light detector operable for producing a first electrical output having a magnitude which is substantially linearly related to the concentration of particles in the medium;
   intercepting the multiply reflected light in a second light detector operable for producing a second electrical output having a generally constant magnitude in relation to the concentration of particles; and
   producing a concentration level signal having a magnitude which is proportional to the ratio of the first electrical output divided by the second electrical output.

2. The method of claim 1, comprising the step of optically deflecting a portion of the beam of light produced by the light source, before it reaches the medium, into the second detector such that the magnitude of the second output is increased, the deflected light being sufficient for linearizing the concentration level signal over a range of concentration levels which extends below about 1%.

3. The method of claim 1, comprising the steps of producing a third electrical output which is proportional to the light produced by the light source and adding the third output to the second output such that the magnitude of the second output is increased in an amount sufficient for linearizing the concentration level signal over a range of concentration levels which extends to below about 1%.

4. The method of claims 1, 2 or 3, further comprising the step of passing the light from the light source into the medium through a transparent window located between the light source and the medium and focusing the light at locations in the medium away from the transparent window.

5. An apparatus for measuring the concentration of suspended particles in a medium, the apparatus comprising:
   a probe in the form of an enclosure which defines an interior space, the probe having an end portion and a transparent window located in the end portion, the transparent window permitting the passage of light therethrough between the probe and the medium and sealing the interior space from the medium;
   a light source in the probe for producing a beam of light for illuminating the medium through the transparent window;
   a first light detector in the probe and positioned therein to intercept directly reflected light from the medium, the first light detector including means for producing a first output of a magnitude which varies generally linearly in relation to the concentration of particles in the medium;
   a second light detector in the probe and positioned for intercepting multiply reflected light from the medium, the second light detector including means for producing a second output having a generally constant magnitude in relation to the concentration of the suspended particles in the medium; and
   means for comparing the first and the second outputs and for producing a concentration level signal having a magnitude which is proportional to the ratio of the first output divided by the second output.

6. The apparatus of claim 5, further comprising a third light detector in the probe and located between the light source and the transparent window, the third light detector operating to detect at least a portion of the light beam from the light source and producing a third output which is proportional to the light intensity of the light source, the apparatus further including means coupled to the second and third light detectors for adding the third output to the second output, the third output having a magnitude which linearizes the concentration level signal at concentration levels which extend to below about 1%.

7. The apparatus of claim 5, further comprising optical reflecting means located in the probe between the light source and the transparent window for diverting a portion of light from its path toward the transparent window and redirecting it toward the second detector to increase the level of the second output, the quantity of light which is redirected being sufficient for linearizing the concentration level signal over a range of particle concentrations which extends to below about 1%.

8. The apparatus of claim 7, in which the optical reflecting means comprises a tip of a screw located in the path of the light, the tip having a reflective surface for reflecting the light toward the second detector, and mirror means disposed in the vicinity of the second detector for reflecting light received from the reflective surface of the tip of the screw into the second detector.

9. The apparatus of claims 6 or 7, in which the first light detector is adapted to respond primarily to light directed along an optical axis thereof, the first detector further including a light opening therein for admitting light into the detector, the opening having a center which is laterally displaced with respect to the optical axis of the first detector.

10. The apparatus of claim 9, further comprising a lens system located in the probe and positioned in the path of the beam of light from the light source, the lens system having a focal length for focusing the light from the light source at points in the medium spaced away from the transparent window.

11. An apparatus for measuring the concentration of suspended particles in a medium, the apparatus comprising:
   a light source for producing a beam of light for illuminating the medium, a portion of the light being reflected back from the medium in the form of directly reflected light and another portion of the light from the light source being reflected back as multiply reflected light, the directly reflected light having an intensity which is proportional to the concentration of suspended particles in the medium and the multiply reflected light having an intensity which is generally constant in relation to the concentration of particles in the medium;

means for measuring the intensity of the directly reflected light and for producing a first output which is proportional thereto;

means for measuring the intensity of the multiply reflected light and for producing a second output which is proportional thereto; and means for producing a concentration level output which is proportional to the ratio of the first and second outputs.

12. The apparatus of claim 11, further comprising means for increasing the magnitude of the second output by a value proportional to the intensity of the light produced by the light source, the value being selected for linearizing the concentration level output over particle concentration levels in the medium which extend to below about 1%.

13. The apparatus of claim 12, in which the means for producing the first output comprises a light detector positioned at the first location with respect to the light source and in the path of the directly reflected light, in which the means for producing the second output comprises at least two light detectors positioned at second locations which are laterally removed from the path of the beam of light from the light source, the second output comprising a combination of respective outputs from each of the at least two light detectors.

14. The apparatus of claim 12, in which the concentration level output is determined by the relationship $c = I_{21} \div (I_{41} + kI_1)$ where c is the concentration level, $I_{21}$ is the first output, $I_{41}$ is the second output, $I_1$ is the intensity of the light from the light source and k is a proportionality constant selected for linearizing c over a range of particle concentrations from about 0–6%.

* * * * *